US010874551B2

(12) United States Patent
Rockley et al.

(10) Patent No.: US 10,874,551 B2
(45) Date of Patent: Dec. 29, 2020

(54) SYSTEMS AND METHODS FOR ENHANCED OCCLUSION REMOVAL DURING OPHTHALMIC SURGERY

(71) Applicant: Johnson & Johnson Surgical Vision, Inc., Santa Ana, CA (US)

(72) Inventors: Paul W. Rockley, Corona Del Mar, CA (US); Han Bor Fam, Singapore (SG)

(73) Assignee: Johnson & Johnson Surgical Vision, Inc., Santa Ana, CA (US)

( * ) Notice: Subject to any disclaimer, the term of this patent is extended or adjusted under 35 U.S.C. 154(b) by 0 days.

(21) Appl. No.: 15/351,276

(22) Filed: Nov. 14, 2016

(65) Prior Publication Data

US 2017/0056245 A1 Mar. 2, 2017

Related U.S. Application Data

(62) Division of application No. 12/018,917, filed on Jan. 24, 2008, now Pat. No. 9,492,318.

(60) Provisional application No. 60/985,571, filed on Nov. 5, 2007.

(51) Int. Cl.
*A61F 9/007* (2006.01)
*A61M 1/00* (2006.01)
*A61F 9/008* (2006.01)

(52) U.S. Cl.
CPC .......... *A61F 9/00745* (2013.01); *A61F 9/008* (2013.01); *A61M 1/0025* (2014.02);
(Continued)

(58) Field of Classification Search
CPC .................. A61F 9/00745; A61F 9/008; A61F 2009/00887; A61F 2009/00872;
(Continued)

(56) References Cited

U.S. PATENT DOCUMENTS 3,693,613 A 9/1972 Kelman
4,597,388 A 7/1986 Koziol et al.
(Continued)

FOREIGN PATENT DOCUMENTS

DE 3822011 A1 1/1990
WO 2008016870 A2 2/2008

OTHER PUBLICATIONS

International Preliminary Report on Patentability and Written Opinion for Application No. PCT/US08/082395, dated May 11, 2010, 7 pages.
(Continued)

*Primary Examiner* — Bhisma Mehta
*Assistant Examiner* — Larry R. Wilson
(74) *Attorney, Agent, or Firm* — Johnson & Johnson Surgical Vision, Inc.

(57) ABSTRACT

A method and apparatus for performing a surgical procedure is provided. The surgical procedure may be a phacoemulsification procedure but other procedures may employ the techniques disclosed. The design includes sensing, within the surgical site, for a material change in fluid flow relative to a predetermined threshold. Upon sensing the fluid flow materially differs from the predetermined threshold, the design temporarily increases aspiration vacuum pressure to the surgical site above a predetermined upper threshold toward a maximum vacuum level. The design applies electrically generated disruptive energy, including but not limited to laser and/or relatively low power ultrasonic energy, to the surgical site from a first point in time measured from when aspiration vacuum pressure is above the predetermined upper threshold to a second point in time where pressure falls below a predetermined lower threshold.

10 Claims, 10 Drawing Sheets

(52) U.S. Cl.
CPC ........ *A61M 1/0031* (2013.01); *A61M 1/0058* (2013.01); *A61M 1/0076* (2013.01); *A61F 2009/0087* (2013.01); *A61F 2009/00872* (2013.01); *A61F 2009/00887* (2013.01); *A61M 2210/0612* (2013.01)

(58) Field of Classification Search
CPC ........ A61F 2009/0087; A61F 9/00736–00763; A61F 9/0079; A61M 1/0058; A61M 2210/0612; A61M 1/0025–0029; A61M 1/0031–0037; A61M 1/0039; A61M 1/0064; A61M 1/0076
See application file for complete search history.

(56) References Cited

U.S. PATENT DOCUMENTS

| | | | |
|---|---|---|---|
| 5,700,240 | A | 12/1997 | Barwick, Jr. et al. |
| 6,007,513 | A | 12/1999 | Anis et al. |
| 7,544,178 | B2 * | 6/2009 | Kadziauskas ....... A61F 9/00745 604/28 |
| 7,670,330 | B2 | 3/2010 | Claus et al. |
| 7,785,316 | B2 | 8/2010 | Claus et al. |
| 8,652,086 | B2 | 2/2014 | Gerg et al. |
| 2004/0092800 | A1 | 5/2004 | MacKool |
| 2005/0118048 | A1 | 6/2005 | Traxinger |
| 2006/0224107 | A1 * | 10/2006 | Claus ................. A61F 9/00745 604/44 |
| 2006/0224143 | A1 | 10/2006 | Claus et al. |

OTHER PUBLICATIONS

International Search Report for Application No. PCT/US08/082395, dated Feb. 10, 2009, 4 pages.

\* cited by examiner

SYSTEMS AND METHODS FOR ENHANCED OCCLUSION REMOVAL DURING OPHTHALMIC SURGERY

CROSS REFERENCE

This application is a divisional of and claims priority to U.S. patent application Ser. No. 12/018,917, filed Jan. 24, 2008, which is a non-provisional of and claims priority to U.S. Provisional Application No. 60/985,571, filed Nov. 5, 2007, the full disclosures of all of which are incorporated herein by reference.

FIELD OF THE INVENTION

The present invention relates generally to the art of ophthalmic surgery, and more specifically to improved systems and methods for removal of occlusions during phacoemulsification procedures.

BACKGROUND OF THE INVENTION

A number of medically recognized techniques are employed for cataractic lens removal, such as phacoemulsification, mechanical cutting or destruction, laser treatments, water jet treatments, and so on.

The phacoemulsification procedure entails making a corneal incision and inserting a phacoemulsification handpiece into the ocular region, where the handpiece includes a needle that is ultrasonically driven in order to emulsify, or liquefy, the lens. Concomitantly, fluid is irrigated into the eye and the irrigation fluid and liquefied lens material are aspirated from the eye. Other medical techniques for removing cataractous lenses also typically include irrigating the eye and aspirating lens parts and other liquids. Additionally, some procedures may include irrigating the eye and aspirating the irrigating fluid without concomitant destruction, alteration or removal of the lens. As is well known, for these various techniques it is necessary to maintain a stable volume of liquid in the anterior chamber of the eye and this is accomplished by irrigating fluid into the eye at the same rate as aspirating fluid and lens material.

During this procedure, it is possible for the aspirating phacoemulsification handpiece to become occluded. This occlusion is caused by particles blocking a lumen or tube in the aspirating handpiece. Such blockage can result in increased vacuum (i.e. increasingly negative pressure) in the aspiration line. The longer the occlusion is in place, the greater the vacuum. Once the occlusion is cleared, a resulting rush of fluid from the anterior chamber into the aspiration line can outpace the flow of new fluid into the eye from the irrigation source. The resulting imbalance of incoming and outgoing fluid can create a phenomenon known as post-occlusion surge or fluidic surge, in which the structure of the anterior chamber moves rapidly as fluid is replaced. Such post-occlusion surge may lead to eye trauma. Current precautions against post-occlusion surge cause cataract surgery to be lengthier and more difficult for the attending surgeon.

Alternate surgical procedures when an occlusion occurs typically include a reduction of aspiration rate to a level less than the irrigation rate before continuing the procedure. This can be accomplished by changing the aspiration rate setting on the system. This, in turn, allows the pump to run slower and the fluid volume in the anterior chamber to normalize. Other alternate surgical systems may employ a restriction in the aspiration circuit to constrict surge flow when an occlusion clears from the aspiration tube. Alternative techniques heretofore utilized to avert blockage issues of the type described include a reduction of vacuum on the occlusion by adjusting system settings. This technique often requires an assistant to perform the actual modification of settings. Still another technique for vacuum control can be accomplished by reducing pressure on a control footpedal or releasing a footpedal altogether. This technique, however, requires a surgeon to discontinue applying ultrasonic power temporarily until the occlusion is either cleared or has been released from the aspirating phacoemulsification handpiece. A disadvantage in releasing the footpedal is the fact that cataract lens material in the aspirating phacoemulsification handpiece may flow back into the eye chamber.

In addition, a combination of the hereinabove recited techniques may be employed as well. However, once an occlusion occurs, the surgeon must identify the cause and then take corrective action. The length of time before the occlusion clears varies. In the time it takes for a surgeon to identify the cause and request corrective action, the occlusion can build sufficient vacuum and then clear, thus resulting in post occlusion surge. As a result, surgeons tend to operate their phacoemulsification systems at lower vacuum levels than otherwise preferable in order to avoid this problem.

A system and method for improving the phacoemulsification procedure, and specifically the removal of occlusions, is addressed in U.S. patent application Ser. No. 11/086,508, filed Mar. 5, 2005, entitled "Application of vacuum as a method and mechanism for controlling eye chamber stability," inventors Michael Claus, et al., published as U.S. Patent Publication 20060224143, the entirety of which is incorporated herein by reference. In the '508 application, duration of an occlusion is determined from the sensed vacuum level (typically a rise in vacuum pressure, (i.e. an increasingly negative pressure)) and/or a sensed flow rate (i.e. a drop in flow rate for a constant vacuum pressure), and in response thereto, at least one of the 1) supply of irrigation fluid, 2) vacuum level, 3) aspiration rate, and 4) power applied to the handpiece is/are controlled.

In particular, when an occlusion is encountered and the monitored vacuum level increases, an occlusion threshold value representing the value of the monitored vacuum level at which the aspiration tube has been completely or substantially (e.g., greater than 50%, and preferably greater than 80%) occluded is assessed. If vacuum reaches a maximum allowable vacuum (Max Vac), the pump is typically stopped. A Max Vac setting may be pre-determined or programmed in the system by a user before or during a surgical procedure. The occlusion threshold may be set at or below the same level as the Max Vac setting. In some embodiments the Max Vac level and occlusion threshold value are set to the same level. Alternately, the occlusion threshold value is set at a percentage (i.e. less than or equal to 100%) of the Max Vac level, such as, for example, in a range between about 20% to about 95%. Alternately, the occlusion threshold may be pre-determined at or programmed to a set vacuum level.

For systems using vacuum pumps (e.g., Venturi pumps), flow rate is monitored instead of vacuum level. When the aspirating handpiece becomes occluded, i.e. partially or fully blocked, flow rate decreases. An occlusion flow rate threshold value may be pre-set in the system or entered into the system. The occlusion flow rate threshold value is the value at which the flow rate is recognized by the system and/or user as indicating that an occlusion has occurred. In other words, as the monitored flow rate decreases, the occlusion flow rate threshold value is the value of the monitored flow rate at which the aspiration tube has been completely or substantially occluded. In embodiments for combination systems using vacuum pumps and flow pumps, one or both of the vacuum level and flow rate may be monitored and the above-described methods of determining occlusion are employed.

Normal operation of the '508 system or systems like the '508 system is shown in FIG. 1. As time progresses and the occlusion encountered, vacuum pressure rises to a Max Vac level, which is sensed, and the vacuum level backed off with ultrasonic energy applied to break up the occlusion. An occlusion ultrasonic energy mode is initiated when the vacuum falls below the occlusion flow rate threshold or "up" threshold, and vacuum maintained at specified levels in an effort to break up the occlusion. Once the occlusion breaks or is believed broken, the occlusion mode is turned off and pressure falls below the Min Vac or "down" threshold. Unoccluded operation resumes, as the occlusion is believed to have broken.

The problem in some instances is that while the occlusion may break, it does not break significantly with only application of phaco power while vacuum is at the upper threshold and thus the occlusion is not fully engaged with or partially released from the phaco tip. Such an inability to aggressively address and remove the occlusion may interfere with further phaco procedures. In other words, application of energy or phaco/ultrasonic power during the period when pressure is dropping from a Max Vac setting is inadequate, or has been deemed of concern by certain surgeons because it simply results in thrusting the phaco tip into an occlusion that is floating or released from the tip. Further, it is noted that ultrasonic energy application can cause excessive heat application to the region, which is undesirable.

While some surgeons have attempted to address this issue by modulating power using a device such as a footpedal, due to the inherent reaction time of the surgeon when the occlusion is encountered, it is difficult or impossible for an individual employing the system to successfully coordinate vacuum and energy application to effectively address the occlusion.

Thus potential issues with a design such as presented in the '508 application include the fact that an ultrasound energy occlusion mode is activated when reaching an intermediate vacuum level or Mid Vac, also known as CASE Vac, after peak vacuum level is reached. In the FIG. 1 arrangement, the vacuum drops below the low vacuum threshold Min Vac before the system can reset back up to or re-achieve Max Vac. The surgeon and system are restricted to the lower vacuum region, in many cases below the Mid Vac or CASE Vac region, and even after the occlusion has been broken, the surgeon must activate ultrasonic energy to cause the occlusion to leave the tip. The net result of this implementation is that the occlusion is inefficiently addressed, inhibiting successful surgery unless significant energy is applied, such as ultrasonic energy, to the ocular region.

It would be desirable to offer a design wherein the foregoing drawbacks could be addressed and a more effective design provided, such as where a surgeon could fully address the occlusion without being forced to address the occlusion in the low pressure unoccluded mode.

SUMMARY OF THE INVENTION

The invention is generally directed to systems and methods for surgery, such as ophthalmic surgery, and systems and methods for performing phacoemulsification procedures using aspiration of the ocular region.

In accordance with one aspect of the present design, the design includes sensing, within the surgical site, for a material change in fluid flow relative to a predetermined threshold. Upon sensing the fluid flow materially differs from the predetermined threshold, the design temporarily increases aspiration vacuum pressure to the surgical site above a predetermined upper threshold toward a maximum vacuum level. The design applies electrically generated disruptive energy, including but not limited to laser and/or relatively low power ultrasonic energy, to the surgical site from a first point in time measured from when aspiration vacuum pressure is above the predetermined upper threshold to a second point in time where pressure falls below a predetermined lower threshold.

Other systems, methods, features and advantages of the invention will be or will become apparent to one with skill in the art upon examination of the following figures and detailed description. It is intended that all such additional systems, methods, features and advantages be included within this description, be within the scope of the invention, and be protected by the accompanying claims.

BRIEF DESCRIPTION OF THE DRAWINGS

A more particular description of the aspects briefly described above will be rendered by reference to specific embodiments thereof, which are illustrated in the accompanying drawings. It should be noted that the components in the figures are not necessarily to scale, emphasis instead being placed upon illustrating the principles of the invention. Moreover, in the figures, like reference numerals designate corresponding parts throughout the different views. However, like parts do not always have like reference numerals. All illustrations are intended to convey concepts, where relative sizes, shapes and other detailed attributes may be illustrated schematically rather than literally or precisely.

DETAILED DESCRIPTION OF THE PREFERRED EMBODIMENTS

Device

Figure 2:
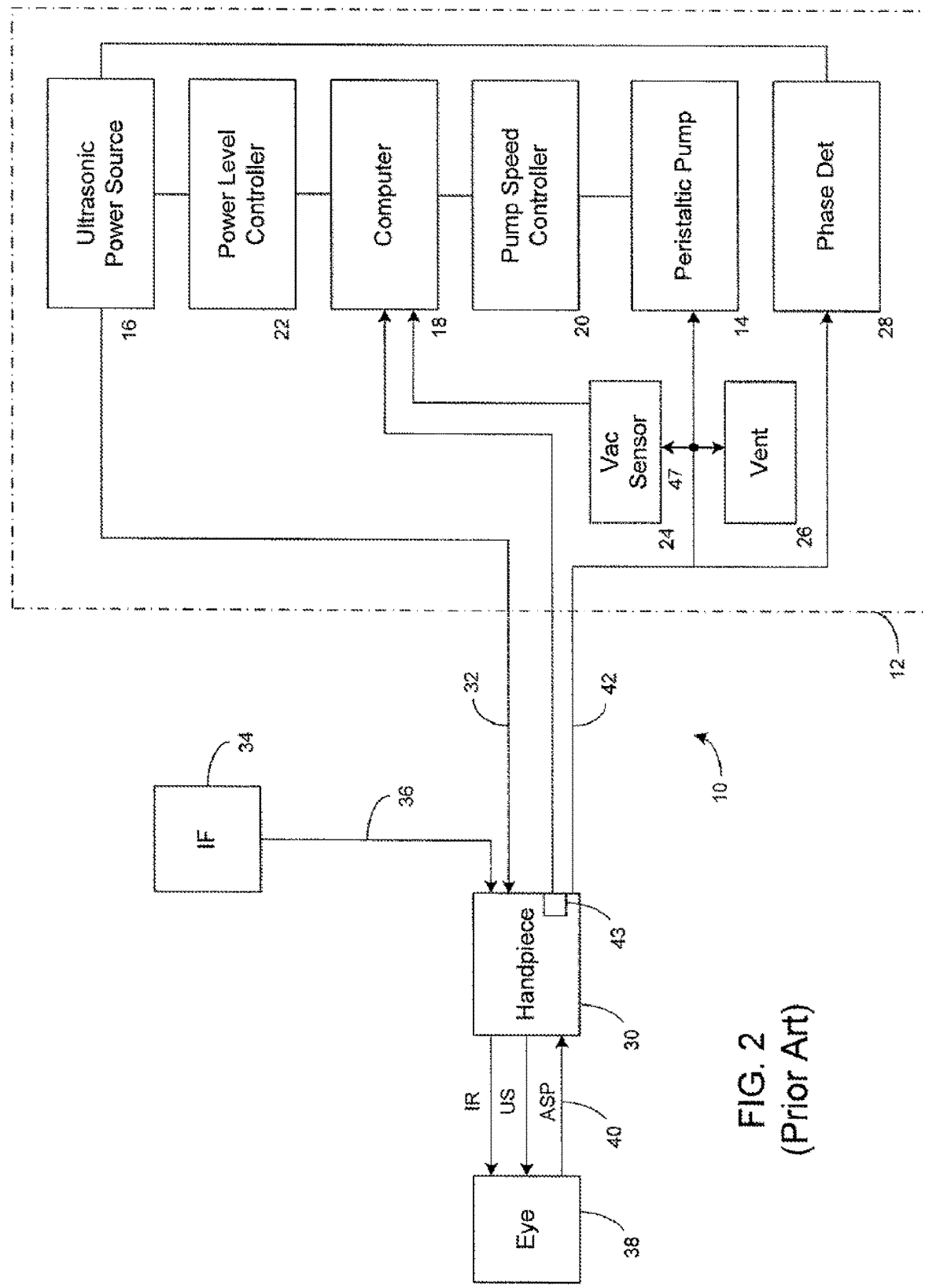
FIG. 2 shows an example of a phacoemulsification system that may employ the present design.

FIG. 2 illustrates a phacoemulsification system in block diagram form, indicated generally by the reference numeral 10. The system has a control unit 12, indicated by the dashed lines in FIG. 2 which includes a variable speed peristaltic pump 14, providing a vacuum source, a source of pulsed ultrasonic power 16, and a microprocessor computer 18 that provides control outputs to pump speed controller 20 and ultrasonic power level controller 22. A vacuum sensor 24 provides an input to computer 18 representing the vacuum level on the input side of peristaltic pump 14. Suitable venting is provided by vent 26.

A phase detector 28 provides an input to computer 18 representing a phase shift between a sine wave representation of the voltage applied to a handpiece/needle 30 and the resultant current into the handpiece 30. The block representation of the handpiece 30 includes a needle and electrical means, typically a piezoelectric crystal, for ultrasonically vibrating the needle. The control unit 12 supplies power on line 32 to a phacoemulsification handpiece/needle 30. An irrigation fluid source 34 is fluidly coupled to handpiece/needle 30 through line 36. The irrigation fluid and ultrasonic power are applied by handpiece/needle 30 to a patient's eye, or affected area or region, indicated diagrammatically by block 38, and may include a lumen (not shown). Alternatively, the irrigation source may be routed to the eye 38 through a separate pathway independent of the handpiece. The eye 38 is aspirated by the control unit peristaltic pump 14 through line/handpiece needle 40 and line 42. A switch 43 disposed on the handpiece 30 may be utilized as a means for enabling a surgeon/operator to select an amplitude of electrical pulses to the handpiece via the computer 18, power level controller 22 and ultrasonic power source 16 as discussed herein. Any suitable input means, such as, for example, a foot pedal (not shown) may be utilized in lieu of the switch 43.

Figure 3:
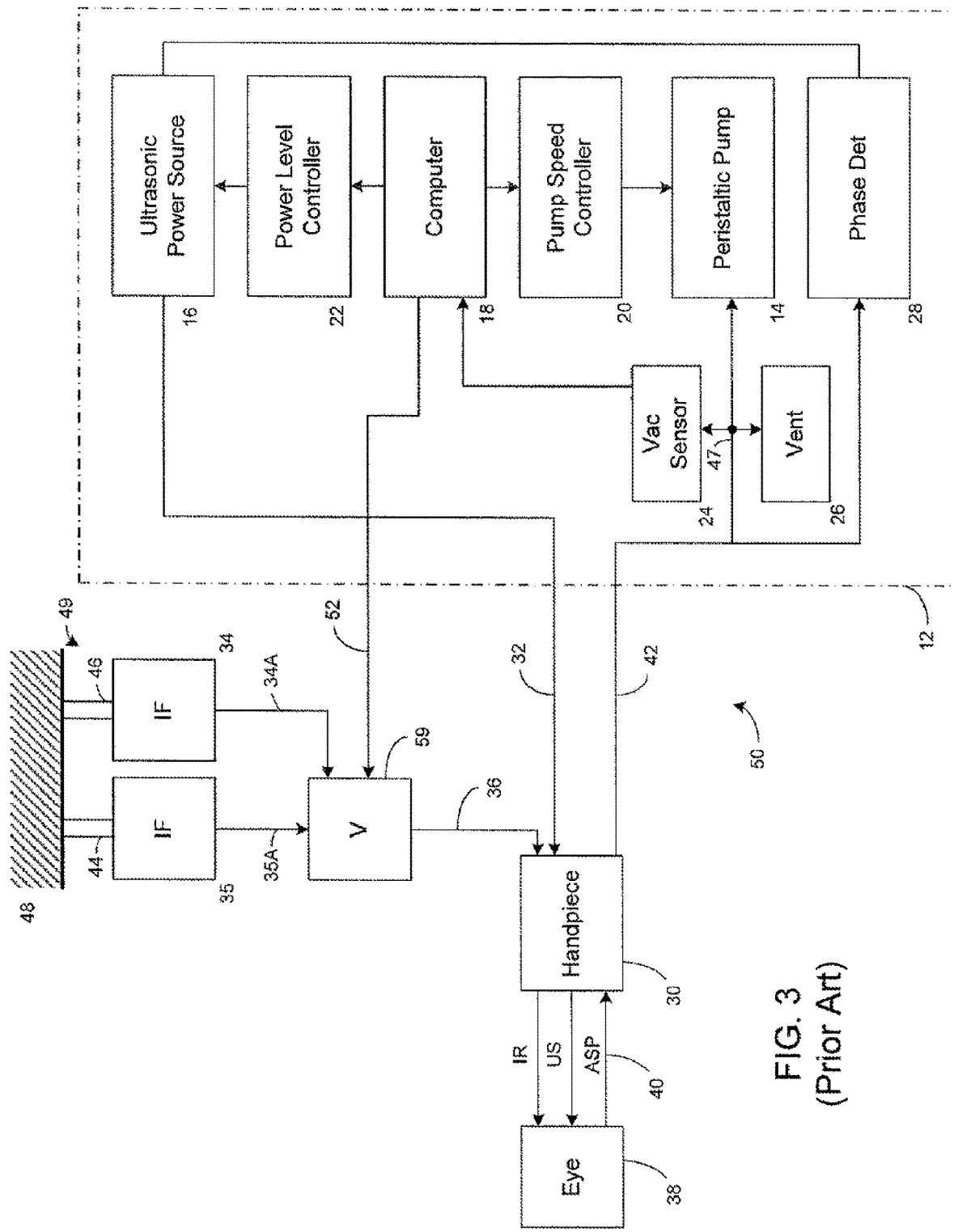
FIG. 3 shows an example of an alternate phacoemulsification that may employ the present design.

FIG. 3 shows an alternative phacoemulsification system 50 incorporating all of the elements of the system 10 shown in FIG. 2, with identical reference characters identifying components, as shown in FIG. 2. In addition to the irrigation fluid source 34, a second irrigation fluid source 35 is provided with the sources 34, 35 being connected to the line 36 entering the handpiece/needle 30 through lines 34a, 35a, respectively, and to a valve 59. The valve 59 functions to alternatively connect line 34A and source 34 and line 35A and source 35 with the handpiece/needle 30 in response to a signal from the power level controller 22 through a line 52.

As shown, irrigation fluid sources 34, 35 are disposed at different heights above the handpiece/needle 30 providing a means for introducing irrigation fluid to the handpiece at a plurality of pressures, the head of the fluid in the container 35 being greater than the head of fluid in the container 34. A harness 49, including lines of different lengths 44, 46, when connected to the support 48, provides a means for disposing the containers 34, 35 at different heights over the handpiece/needle 30.

The use of containers for irrigation fluids at the various heights is representative of the means for providing irrigation fluids at different pressures, and alternatively, separate pumps may be provided with, for example, separate circulation loops (not shown). Such containers and pumps can provide irrigation fluid at discrete pressures to the handpiece/needle 30 upon a command from the power controller 22.

Fluid Operation/Aspiration

Figure 4:
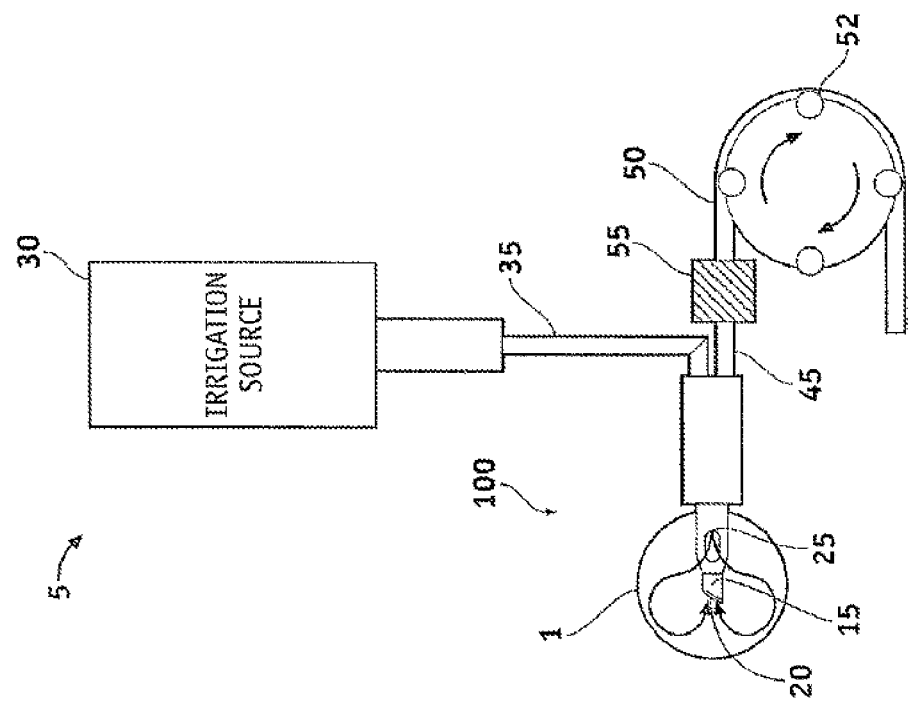
FIG. 4 is an example of a peristaltic pump.

Aspiration can be achieved with a variety of different aspiration pumps 40 known in the art. The two most common types are (1) volumetric flow or positive displacement pumps (such as peristaltic or scroll pumps) and (2) vacuum-based pumps (such as venturi, diaphragm, or rotary-vane pumps). Each type has its own general advantages and disadvantages. Turning to FIG. 4, an example peristaltic flow pump 50 is illustrated. In this configuration, the aspiration line 45 is in direct contact with a rotating pump head 50 having rollers 52 around its perimeter. As the pump head 50 rotates clockwise, the rollers 52 press against the line 45 causing fluid to flow within the line 45 in the direction of the rollers 52. This is referred to as a volumetric flow pump because the pump 50 directly controls the volume or rate of fluid flow. An advantage with this type of pump 50 is that the rate of fluid flow can be easily and precisely controlled by adjusting the rotational speed of the pump head 50.

Figure 5:
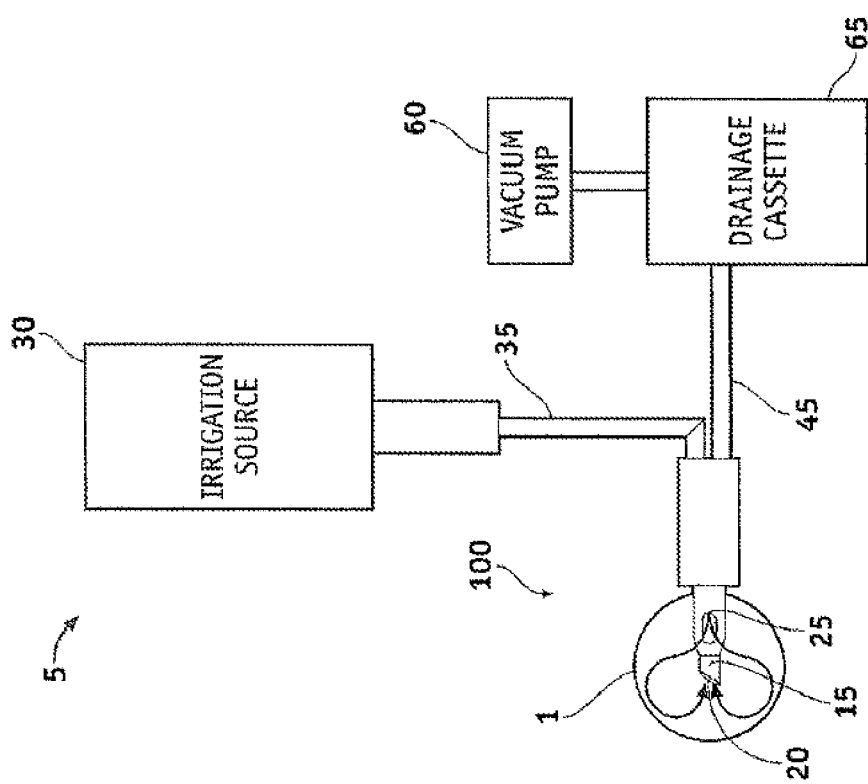
FIG. 5 shows one example of a vacuum based pump.

FIG. 5 illustrates an example vacuum-based pump 60. This type of pump indirectly controls fluid flow by controlling the vacuum within the fluidic circuit. For example, the vacuum-based pump 60 can be a pneumatic pump (e.g., a venturi pump) that creates a lower pressure in a drainage cassette reservoir 65 that causes the fluid to flow from the eye into the aspiration line 45 and into the drainage cassette reservoir 65. Thus, instead of pushing fluid through the aspiration line 45 like the flow pump 50, the fluid is essentially pulled by vacuum through the line 45. The rate of fluid flow generated by a vacuum-based pump is generally higher than the rate of fluid flow generated by a volumetric flow based pump; however, current systems and methods for controlling the rate of volumetric flow for the vacuum-based pump, which typically involve manually adjusting the operative vacuum level, are imprecise, which raises safety and efficacy concerns.

As is well known, for these various surgical techniques it is necessary to maintain a stable volume of liquid in the anterior chamber of the eye and this is accomplished by irrigating fluid into the eye at the same rate as aspirating fluid and lens material. For example, see U.S. Pat. No. 5,700,240, to Barwick et. al, filed Jan. 24, 1995 ("Barwick") and U.S. patent application Ser. No. 11/401,529 to Claus et. al, filed Apr. 10, 2006 ("Claus"), which are both hereby incorporated by reference in their entirety. During phacoemulsification, it is possible for the aspirating phacoemulsification handpiece 100 to become occluded. This occlusion is caused by particles blocking a lumen or tube in the aspirating handpiece 100, e.g., the aspiration port 20 or irrigation port 25. In the case of volumetric flow based pumps, this blockage can result in increased vacuum (i.e. increasingly negative pressure) in the aspiration line 45 and the longer the occlusion is in place, the greater the vacuum if the pump continues to run. In contrast, with a vacuum-based pump, this blockage can result in a volumetric fluid flow drop off near the aspiration port 20. In either case, once the occlusion is cleared, a resulting rush of fluid from the anterior chamber into the aspiration line 45 can outpace the volumetric flow of new fluid into the eye 1 from the irrigation source 30.

The resulting imbalance of incoming and outgoing fluid can create a phenomenon known as post-occlusion surge or fluidic surge, in which the fluid in the anterior chamber of the eye is removed faster than can be replaced. Such post-occlusion surge events may lead to eye trauma. The most common approach to preventing or minimizing the post-occlusion surge is to quickly adjust the vacuum-level or rate of fluid flow in the aspiration line 45 and/or the ultrasonic power of the handpiece 100 upon detection of an occlusion. Many surgeons rely on their own visual observations to detect the occlusion; however, because of the unpredictable and time-sensitive nature of the problem, a reliable computer-based detection and response system is preferable to provide a faster reaction time.

For current systems with volumetric flow pumps 50, if an occlusion occurs, the flow rate will decrease at the aspiration port 20 and the vacuum level within the aspiration line 45 between the pump 50 and the handpiece 100 will increase. Thus, a computer-based system (not shown) can utilize a vacuum sensor 55 placed on the aspiration line 45 to detect the vacuum increase and respond accordingly (an example of such a system is described in "Barwick" and "Claus"). For current systems with vacuum-based pumps 60, however, the vacuum level within the aspiration line 45 is tied to the vacuum power generated by the pump 60 and thus, may not be an effective indicator of whether an occlusion has occurred. Nonetheless, vacuum-based pumps may still be preferred in circumstances where high aspiration flow rate is desirable. Accordingly, an improved system and method for phacoemulsification having the advantages of both volume-based and vacuum-based pumps is desirable.

Control

The present design applies to controlling at least one of: 1) the supplied irrigation fluid, 2) vacuum, 3) aspiration rate, and 4) the power applied to a handpiece in an ophthalmic surgery procedure to facilitate removal of an occlusion preferably using little or no phaco power but an alternate lower power application or device. The aspiration force may be provided by any type of fluid pump, including flow pumps and vacuum pumps as described above.

When an occlusion occurs, the duration of the occlusion is determined in flow pump systems by measuring the amount of time starting from the time when the monitored vacuum rises above an occlusion threshold value. In vacuum pump systems, occlusion is measured as when the monitored flow rate falls below an occlusion flow rate threshold value. After the passing of a programmed or predetermined period of time, (herein referenced as a threshold time ($t_T$)), the phaco system has typically reduced the maximum allowable vacuum level to a user programmable new maximum vacuum (Low Vac) level. This causes less vacuum around the particle occluding the aspiration handpiece. Reducing vacuum may occur through various known actions, such as, for example: by venting the vacuum; by allowing air or fluid into the vacuum area (e.g., between the occlusion and the pump); by reversing pump flow; and/or by the phaco system automatically lowering the vacuum setting, as differentiated from the surgeon manually lowering the vacuum setting. Such actions change the state of vacuum pumps such as a Venturi pump. The threshold time ($t_T$) is typically in a range between tens of milliseconds and hundreds of milliseconds, and preferably in a range between about 50 milliseconds and about 300 milliseconds. A trigger value may be set to indicate that the maximum allowable vacuum level has been reduced to a lower level (i.e. Low Vac). The system then returns to monitoring vacuum as treatment continues.

During this period of time, there has been no change in the surgeon's foot pedal (not shown) position nor has an assistant been required to modify any setting on the system. Such manual alterations can be difficult to perform with a high degree of accuracy. Changes to the vacuum settings can be performed by altering the setting using a footpedal or switch on the phaco machine, but this is cumbersome and difficult and can result in delayed adjustments. Accordingly, the present design can reduce the need for manual input and accordingly enables the physician to concentrate on the procedure. The physician mandates the desired settings, and as a result certain predetermined conditions trigger certain system events, such as application of disruptive energy at a certain time, resulting in a reduced need for surgeon input. The result is an increase in the physician's efficacy and the ability to perform a better overall procedure.

The Low Vac level may be set to a level with sufficient vacuum to hold the particle and allow the surgeon to separately or in combination: 1) vary phaco power (or more generally the power to the handpiece surgical mechanism (i.e. laser, cutters, etc.), 2) vary the aspiration rate, and/or 3) vary the irrigation rate as required to clear the occlusion. The method will typically not allow the vacuum level to rise above the Low Vac level until the occlusion has cleared.

When the occlusion is cleared, the system operates at the Low Vac level where the potential for post occlusion surge is minimized. In addition, in flow pumps (e.g., peristaltic pumps) after the occlusion is cleared, the actual vacuum level in the aspiration line will drop. In vacuum pumps (e.g., Venturi pumps), the flow rate will rise after the occlusion has cleared. In combination systems using both types of pumps, either or both a vacuum drop or a flow rate increase may be measured after the occlusion is cleared.

In one embodiment, the vacuum drop in a flow-type pump system is identified by determining when it falls below a user programmable or pre-set minimum vacuum threshold (Low Threshold), at which point an original user-programmed maximum allowable vacuum aspiration level (Max Vac) is typically reinstated. In an alternate embodiment employing a vacuum pump, the flow rate increase is identified by determining when the flow rate rises above a user programmable or pre-set minimum flow rate threshold (Low Flow Rate Threshold), at which point an original user-programmed maximum allowable vacuum aspiration level (Max Vac) is typically reinstated. For a flow pump system, when the monitored vacuum is below the occlusion threshold value, the system checks to determine if Low Vac is available. If not, then normal vacuum and fluid functions are continued. If Low Vac is the current setting and the monitored vacuum level is below a Low Threshold, Max Vac is re-set. If monitored vacuum is not below Low Threshold, then vacuum monitoring continues. In vacuum pump embodiments, when monitored flow rate is above the occlusion flow rate threshold, the system checks to determine if Low Vac is set, and if not, then normal vacuum and fluid functions are continued. If Low Vac is the current setting, then Max Vac is re-set.

Figure 6:
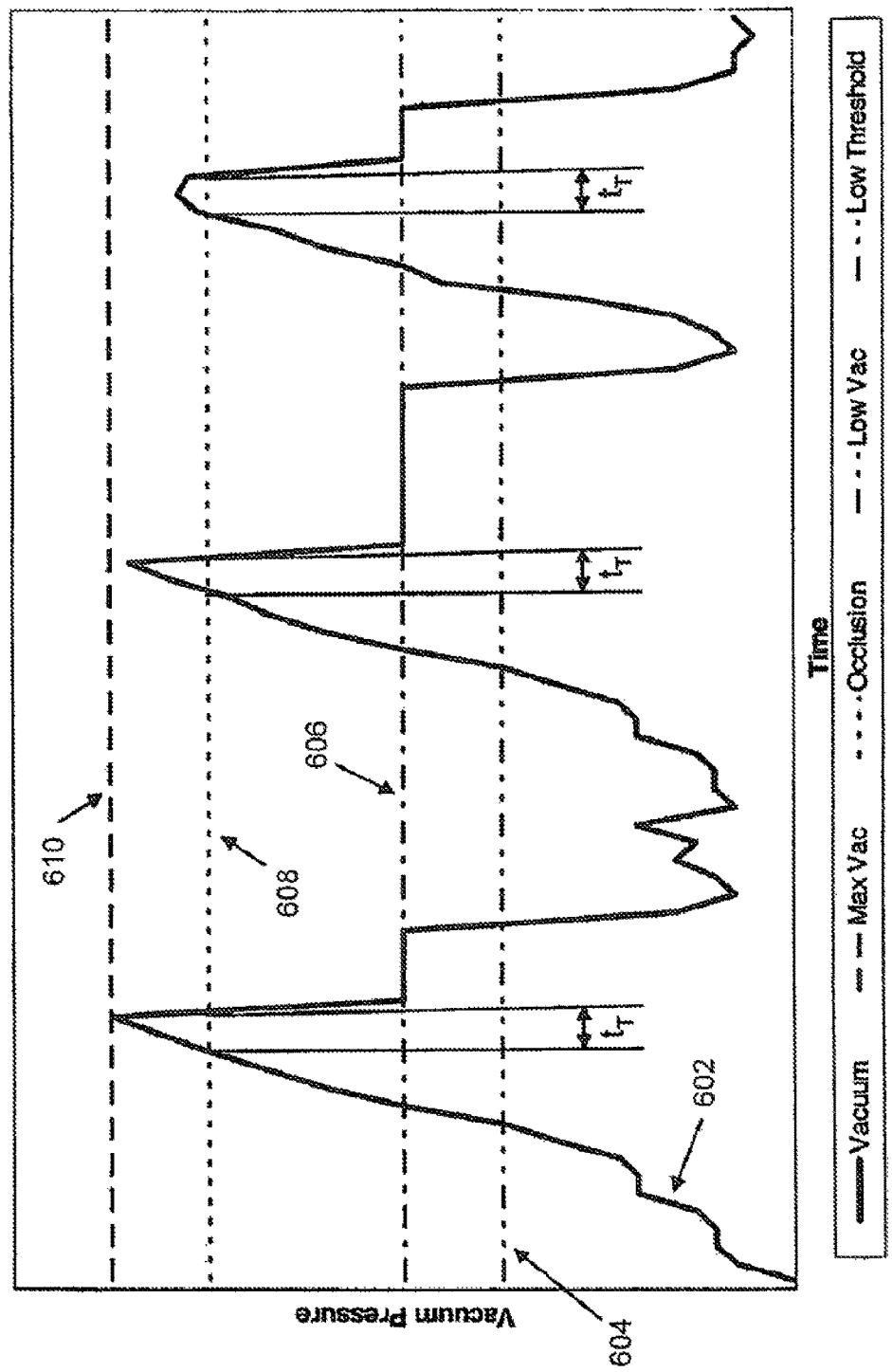
FIG. 6 is a graphical example of monitored vacuum levels in known available systems, such as the '508 system discussed.
Figure 7:
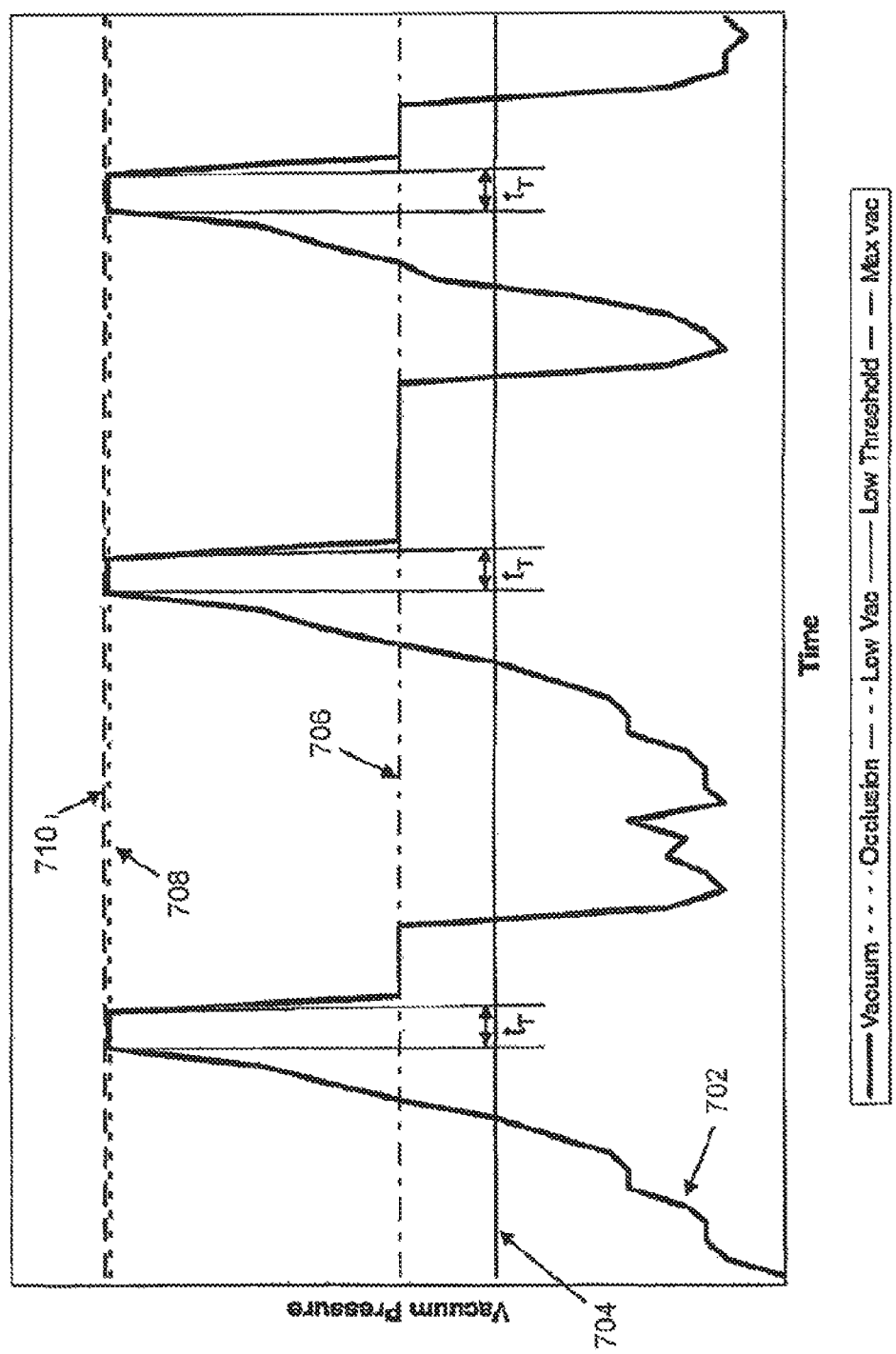
FIG. 7 illustrates a design similar to FIG. 6 wherein Max Vac value and the occlusion threshold value are pre-determined or programmed at or very near the same level.

FIGS. 6 and 7 depict graphical examples of monitored vacuum levels in previously available systems, such as the '508 system previously described. FIG. 6 shows an example in which Max Vac (610) is set at a level above occlusion threshold (608). Low Vac (606) and Low Threshold (604) are also pre-determined or programmed. The monitored vacuum is line 602. Starting at the left side of FIG. 6 and following monitored vacuum 602 to the right, as vacuum 602 rises during a procedure and crosses occlusion threshold 608, the system recognizes that an occlusion has begun and a timer begins measuring the time. If vacuum 602 reaches the Max Vac level (not shown), then the pump may be reversed or vented and the maximum allowable vacuum level may be re-set to Low Vac. If Max Vac is not exceeded and once the measured time has passed the threshold time ($t_T$), then the maximum allowable vacuum level is dropped to the Low Vac level, again with the pump being reversed or vented, thereby reducing the monitored vacuum 602. Alternately, the Low Vac may be set without waiting for a threshold time to pass, in which case a timer would not be needed. As the occlusion is cleared by whatever means, vacuum 602 begins to drop again until it falls below Low Threshold (604). At that point, the system recognizes that the occlusion has been cleared, and Max Vac is re-set as the maximum allowable vacuum level. In this previous design, the monitored vacuum level 602 typically stays at the lower level in flow pump systems until another occlusion is encountered. When another occlusion is encountered, the vacuum 602 begins to rise again and the process stated above begins anew.

FIG. 7 shows a similar example to that of FIG. 6, with the difference that the Max Vac value (710) and the occlusion threshold value (708) are pre-determined or programmed at or very near the same level. Low Vac (706) and Low Threshold (704) are also pre-determined or programmed. The monitored vacuum line on the graph is 702. Starting at the left side of FIG. 7 and following monitored vacuum 702 to the right, as vacuum 702 rises during a procedure and reaches occlusion threshold 708 and Max Vac level 710, the system recognizes that an occlusion has occurred and a timer begins measuring the time. Additionally, the pump is typically vented or reversed and the maximum allowable vacuum level is re-set to Low Vac, thereby reducing the monitored vacuum 702. In some embodiments, the Low Vac is not set until the threshold time has been reached. Alternately, the Low Vac may be set without waiting for a threshold time to pass, in which case a timer would not be needed. As the occlusion is cleared by whatever means, vacuum 702 begins to drop again until it falls below Low Threshold (704). At that point, the system recognizes that the occlusion has been cleared, and Max Vac (710) is re-set as the maximum allowable vacuum level. The monitored vacuum level 702 typically stays at the lower level in flow pump systems until another occlusion is encountered. When another occlusion is encountered, the vacuum 702 begins to rise again and the process stated above begins anew. Note that graphical representations of embodiments including vacuum pumps wherein flow rate is sensed and used to control vacuum generally look like inverted versions of FIGS. 6 and 7 with the y-axis showing flow rate and without a Max Vac value.

The above description presents two vacuum levels (i.e. Max Vac and Low Vac), however other designs may include various intermediate levels and settings. For example, a middle vacuum level (Mid Vac or CASE Vac) between Max Vac and Low Vac can be pre-determined or programmed. In such an embodiment, once monitored vacuum has risen above occlusion threshold for a set threshold period of time, the maximum allowable vacuum level is set to Mid Vac. If the occlusion is not cleared at Mid Vac after a second threshold period of time, then the maximum allowable vacuum level is set to Low Vac and held there until the occlusion is cleared. After occlusion clearance (i.e. once monitored vacuum has fallen below a Low Threshold), the maximum allowable vacuum level may be re-set to either Mid Vac or Max Vac.

By having one or more intermediate vacuum levels, a user has more control over the vacuum levels as well as the potential surge characteristics once an occlusion is cleared. Once an occlusion has been determined, the system may automatically begin lowering the maximum allowable vacuum level incrementally by pre-determined or programmed increments until the occlusion is cleared. In this arrangement, the vacuum could be maintained as close to Max Vac as possible throughout the procedure. These alternate implementations are equally applicable to flow pump systems or combination pump systems.

One advantage of such operation is that surgeons can more safely and effectively utilize the full range of aspiration rates, vacuum pressures and flow rates available on typical surgical devices. For example, in typical phacoemuslification devices, the aspiration mechanisms may allow for vacuum or suction pressures during normal operation up to 650 mmHg or more. Typical current suction pressures may be in the range of 300 mmHg. Often, surgeons use the low end or middle of the available aspiration ranges in order to avoid unsafe fluidic surges during occlusion events. However, this means that they are typically treating at a slower rate because of the reduced aspiration flow. Because the system responds so quickly, the result is an increase in the efficacy of the surgeon while concurrently reducing overall surgical time.

Enhanced Performance

Figure 1:
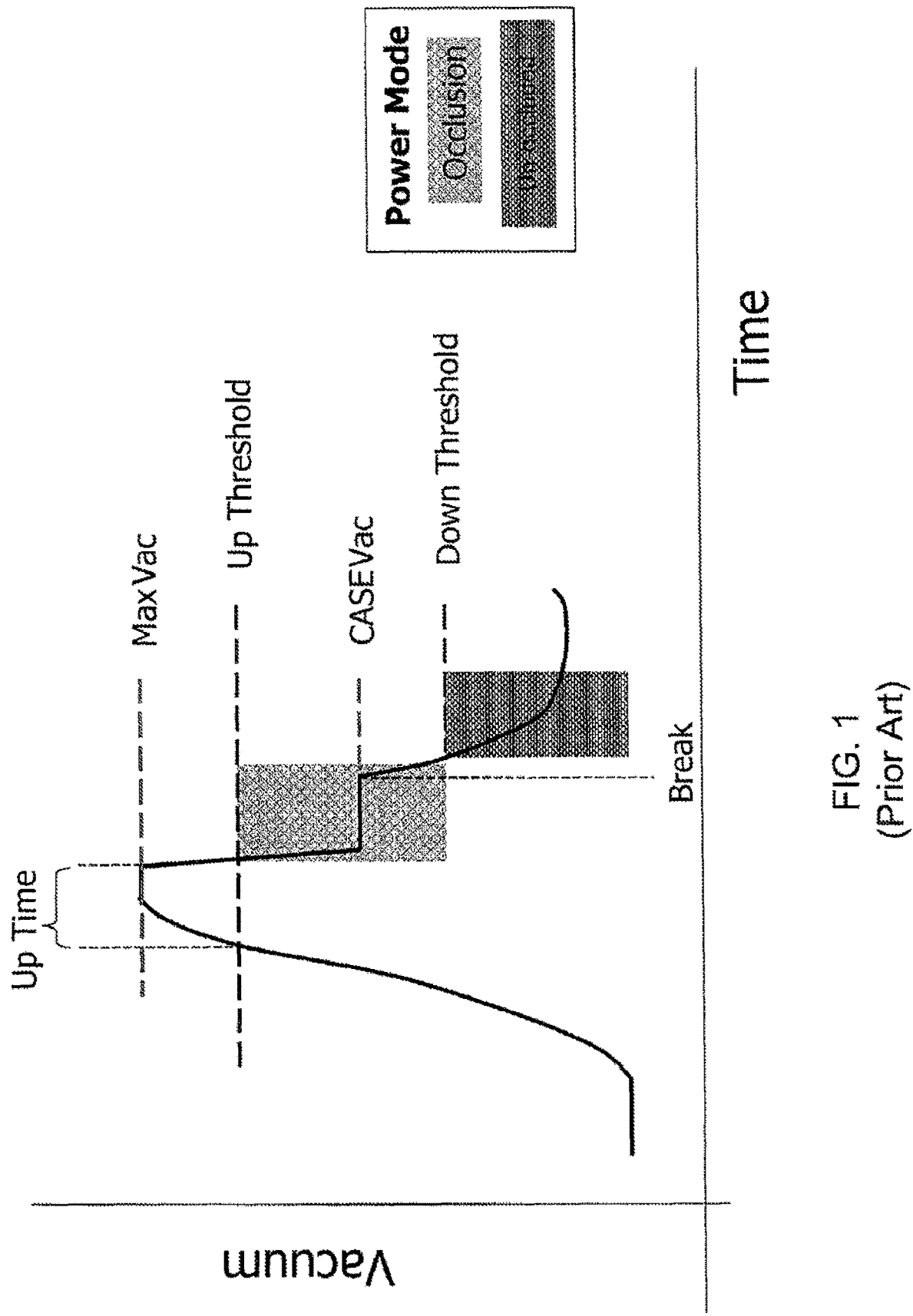
FIG. 1 illustrates a representative vacuum flow profile when an occlusion is encountered according to previous designs.

As previously discussed, the foregoing tends to stress the fragment or occlusion before the application of ultrasonic power, wherein a burst of ultrasonic energy, or phaco power, is applied as shown in FIG. 1, namely once vacuum pressure is below the up or upper threshold. This results in either fragmenting of the occlusion, which is undesirable, or excessive application of energy to the ocular region, or both, and can be undesirable to many surgeons.

Figure 8:
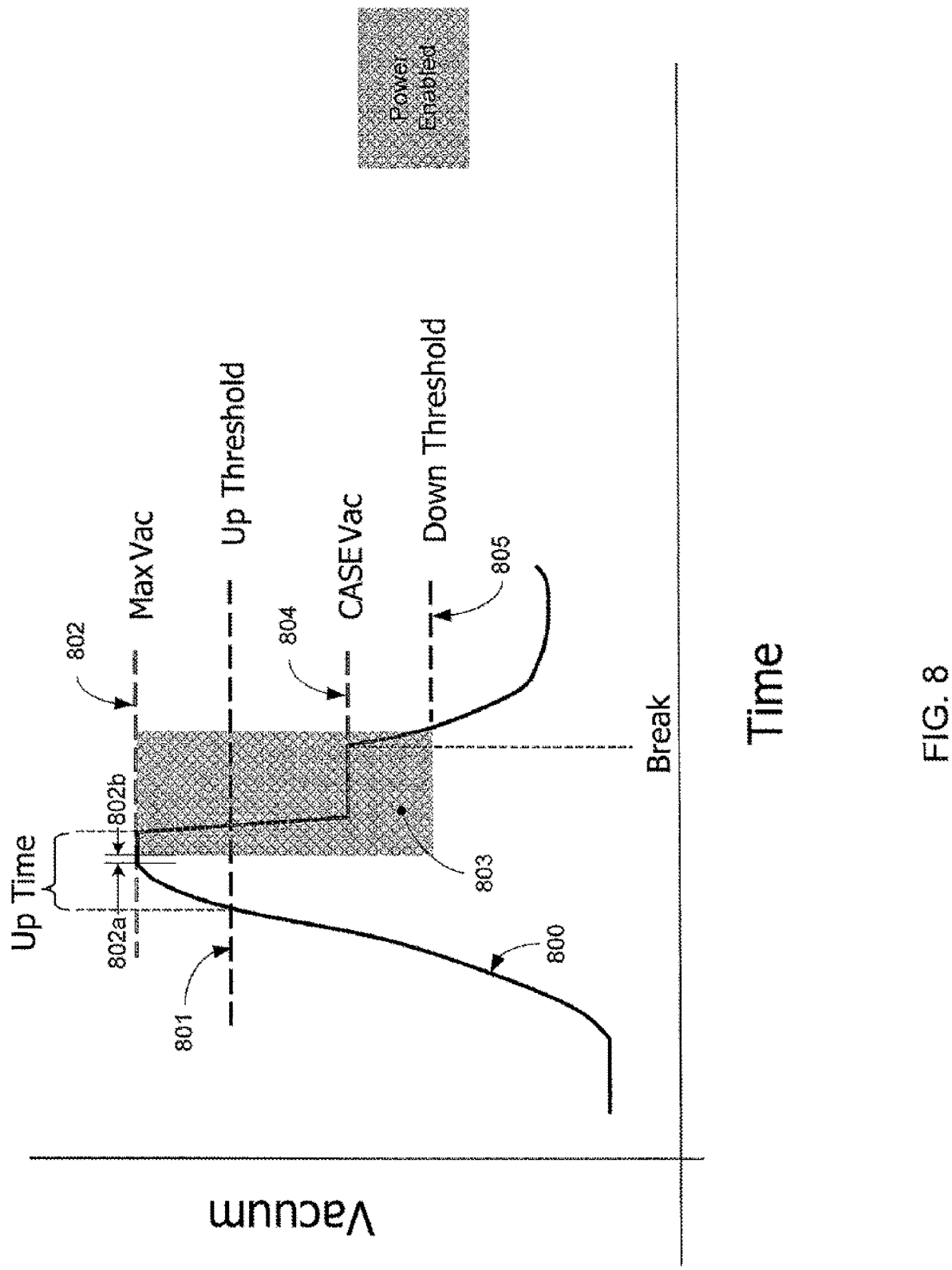
FIG. 8 shows enhanced vacuum performance used to better remove occlusions without applying relatively significant energy to the surgical region or site.

FIG. 8 illustrates enhanced performance used to better remove occlusions without applying relatively significant energy to the ocular region, including application of ultrasound energy during the period after the vacuum attains the Max Vac level. FIG. 8 represents application of alternate disruptive energy, sufficient to address the occlusion without stressing the fragment.

In simple terms, the present design applies disruptive energy in some form earlier in the occlusion period, essentially holding the occlusion close to the tip during a vacuum phase while applying disruptive energy at a desirable level, effectively holding the occlusion while applying significant force to the occlusion, increasing the likelihood that the occlusion is broken. While ultrasound energy may be applied, it is to be understood that other types of disruptive energy or power may be applied, but typically electrically generated disruptive energy or power, including but not limited to laser energy, mechanical cutting devices, high pressure water or liquid pulses, electrical pulses such as RF pulses, or other mechanically or electrically generated disruptive energy. Certain types of mechanical or electrically generated disruptive energy may work better in certain applications than others. Laser energy may be provided in various forms, including but not limited to ND-YAG laser energy.

From FIG. 8, as contrasted with FIG. 1, all energy application is disabled until the signal representing vacuum level 800 approaches Max Vac line 802, representing the Maximum Vacuum level attainable by or permitted by the phaco machine. Disabling energy application, including ultrasonic energy application, prevents chattering of the phaco tip and premature occlusion break. Premature occlusion break can result in energy application to a broken occlusion, essentially wasting energy after max vacuum is achieved. The rise in vacuum pressure from the up threshold 801 to Max Vac 802 occurs when the tissue is being held tightly to the phaco tip. Max Vac is maintained for a period of time, on the order of approximately zero to three seconds, but frequently less than two seconds. At a certain point in time after reaching Max Vac, such as at points 802a or 802b (e.g. a first point in time), settable by the user, operator, or manually set within the system, a power enabling mode begins (e.g. a third point in time) by applying disruptive energy, such as ultrasonic energy, to the tissue. Point 802a represents at the time Max Vac 802 is achieved, while point 802b represents a predetermined time interval after Max Vac is achieved or substantially achieved, such as within a threshold. Such energy or power application, shown as region 803, may therefore begin prior to, at the time of, or shortly after vacuum pressure reaches Max Vac 802. This causes application of energy to the occlusion while at Max Vac 802 from a first point in time (e.g. 802a or 802b) to a second point in time and trailing downward, through up threshold 801 and CASE Vac 804 as shown. The second point in time occurring after the third point in time when disruptive energy is applied. The occlusion typically breaks during this period and pressure drops below down threshold 805. At a fourth point in time energy or power application 803 is ceased after the aspiration vacuum falls below the up threshold 801 and CASE Vac 804. As shown in FIG. 8, the fourth point in time occurs after the aspiration vacuum falls below the CASE Vac 804.

Such sequencing as shown in FIG. 8 results in relatively low power usage, as compared against the ultrasonic energy application shown in FIG. 1, by relying on the disruptive advantage of the vacuum and using the local disruptive effects of the vacuum, acting only on the tissue as opposed to the wider range of energy application in the ultrasonic or laser energy application This automatic processing and power application monitoring based on reaching Max Vac 801 tends to improve response time, and cannot interrupt vacuum pressure and thus cause a surge in pressure, which is undesirable. The reduced application of power or energy as shown in FIG. 8 tends to reduce the heat applied to the region and reduces the risk of collateral tissue damage. Further, no additional surgeon input or special technique or equipment modulation is needed, resulting in a shorter time period and less overall power in addressing the occlusion.

Different power modalities and different vacuum rise zones may be employed, such as applying energy before or after the period (points 802a and 802b) shown in FIG. 8. By utilizing the present design, higher aspiration rates and vacuum levels may be used without fear of fluidic surges. In operation, the present design provides a series of disruptive energy pulses, such as laser or ultrasonic pulses, interspersed or coexistent with vacuum sensing, continuing until the sensor indicates occlusion breaking.

Note that while the vacuum level 800 in FIG. 8 indicates that Max Vac 802 is attained, such as at points 802a or 802b, in operation the Max Vac value may not precisely be attained, but some level very close to Max Vac 802 attained at the time energy application begins. Transient circumstances can cause the vacuum level 800 to vary at any time during a normal procedure, and the present design is not limited to precisely attaining Max Vac 802 before disruptive energy or power is applied. Further, while the system may apply the electrically generated disruptive energy at a time such as points 802a or 802b, measured from when vacuum level 800 achieves Max Vac 802 or has achieved Max Vac 802 for a period of time or has achieved an average level of Max Vac for a period of time, or some predetermined level, such as a percentage of Max Vac 802, or some other time measurement, the application of disruptive energy may occur using some other measurement, such as a predetermined amount of time after the upper threshold 801 has been achieved. Any type of time measurement or condition measurement wherein vacuum level 800 has achieved the upper threshold 801 and is progressing toward or has achieved Max Vac 802 may be employed in the current design.

Figure 9:
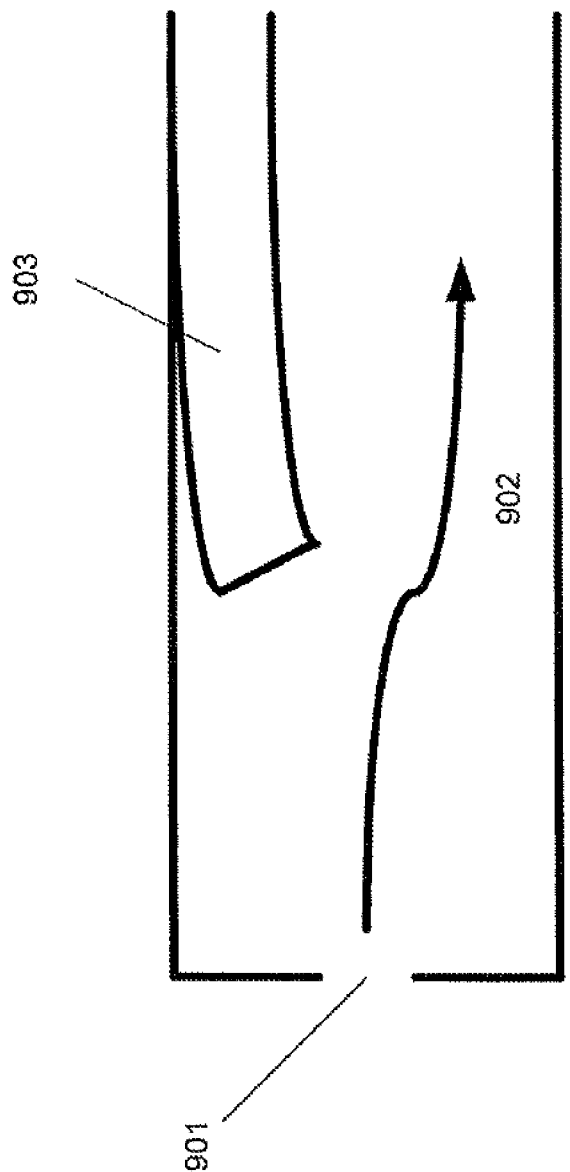
FIG. 9 is a drawing of a tip of a handpiece that could be employed to deliver disruptive mechanical energy, such as laser energy, to the surgical site for purposes of removing or addressing an occlusion.

Regarding application of laser power or energy, a laser assisted aspiration handpiece is a design similar to the known phaco handpiece, but may have an energy generator installed or provided, i.e. a laser emitter at or near the phaco tip. A drawing of a tip is presented in FIG. 9, with aspiration port 901 feeding into aspiration path 902, and quartz fiber or some other known laser tip may be employed as device 903 representing the laser emitter. Other designs may be employed to effectuate the functionality described herein.

Figure 10:
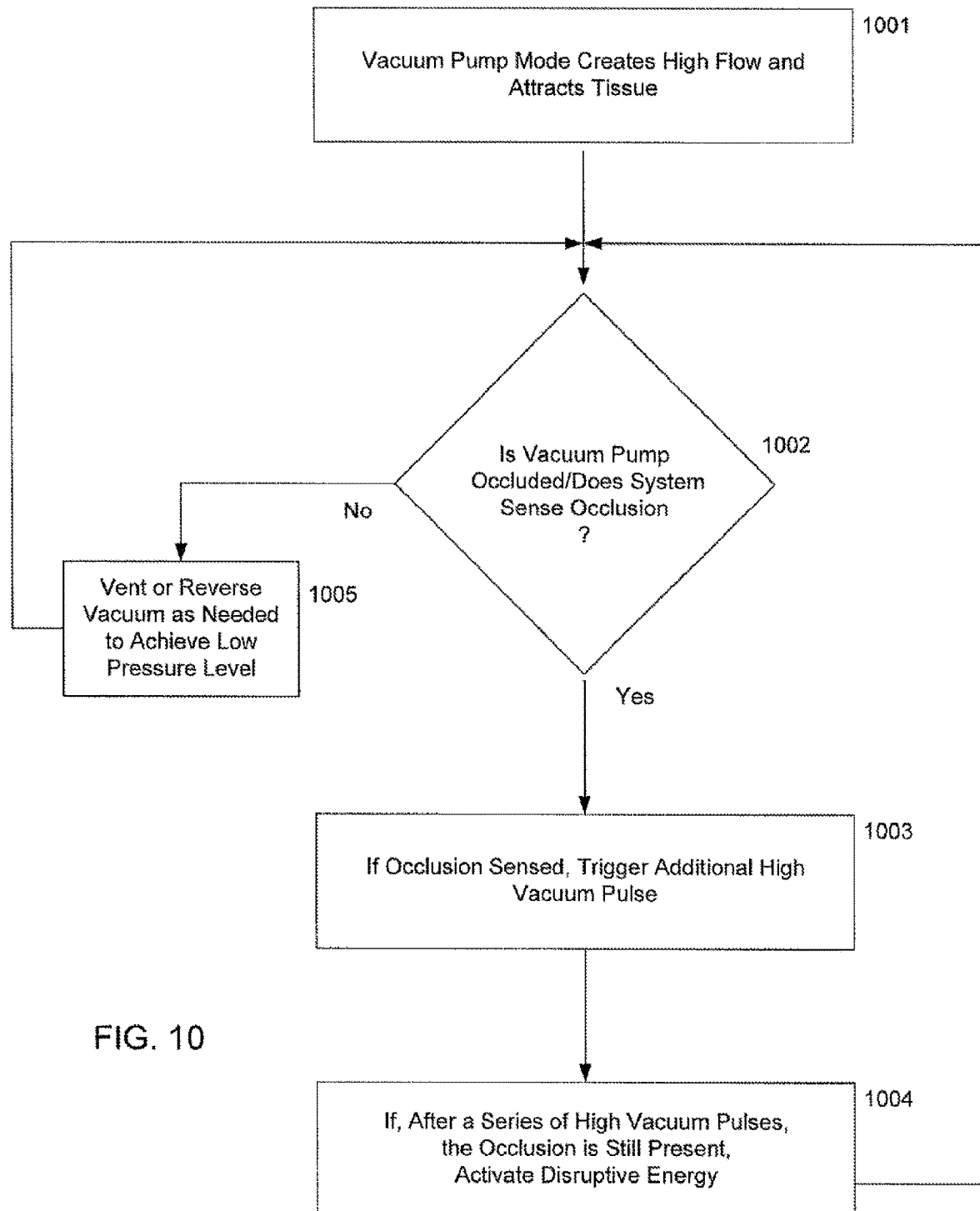
FIG. 10 illustrates one aspect of sequencing of the present design.

Sequencing of the design progresses in one embodiment as shown in FIG. 10. At point 1001, the vacuum pump mode (venturi/rotary) is used to create high flow and attract tissue. The system then determines whether the vacuum pump line has become occluded by sensing an occlusion as shown at point 1002. If an occlusion is sensed at point 1002, the system triggers an additional high vacuum pulse at point 1003, and multiple such pulses may be employed. At point 1004, if, after a series of high vacuum pulses, the occlusion is still present, then the system activates disruptive energy to break up tissue at the tip. The system activates disruptive energy after a predetermined period of time measured from either achieving the upper threshold, or Max Vac, or upon achieving some other desired criteria. Again, the disruptive energy could be ultrasonic energy, laser energy, or other electrically generated disruptive energy. The system thereupon returns to point 1002 to sense for an occlusion. If the vacuum pump line is not occluded and the system does not sense an occlusion at point 1002, including when an occlusion break is sensed or vacuum pressure is rising, the system at point 1005 vents or reverses the pump to put fluid back in the aspiration line to reduce the vacuum to a low, non-surge level. The sequence repeats until all or substantially all tissue is removed.

Note that while much of the sensing in the foregoing discussion of FIG. 10 and throughout this discussion represents sensing of vacuum pressure in an aspiration line, the present design may sense changes in irrigation pressure as well and act based on material changes in irrigation pressure. For example, occlusion may be sensed by interruption or change in the irrigation fluid flow through the surgical site. In general, the present design senses changes in fluid flow for fluid passing through the ocular region or surgical site, whether being provided to or being received from the ocular region or surgical site. Controlling fluid flow to and from the eye and sensing fluid flow is shown, for example, in U.S. patent application Ser. No. 10/692,832, entitled "Method for Controlling Fluid Flow to and from An Eye During Ophthalmic Surgery," inventors Kenneth Kadziauskas et al., filed Oct. 24, 2003, the entirety of which is incorporated herein by reference.

Also, while the present discussion contemplates or suggests peristaltic pump usage in sensing functions, it is to be understood that a venturi pump may alternately be employed. Discussion of operation of a venturi pump in power and flow rate control are discussed in, for example, U.S. patent application Ser. No. 11/530,306, entitled "System and Method for Power and Flow Rate Control," inventors James Gerg et al., filed Sep. 8, 2006, the entirety of which is incorporated herein by reference.

Figure 11:
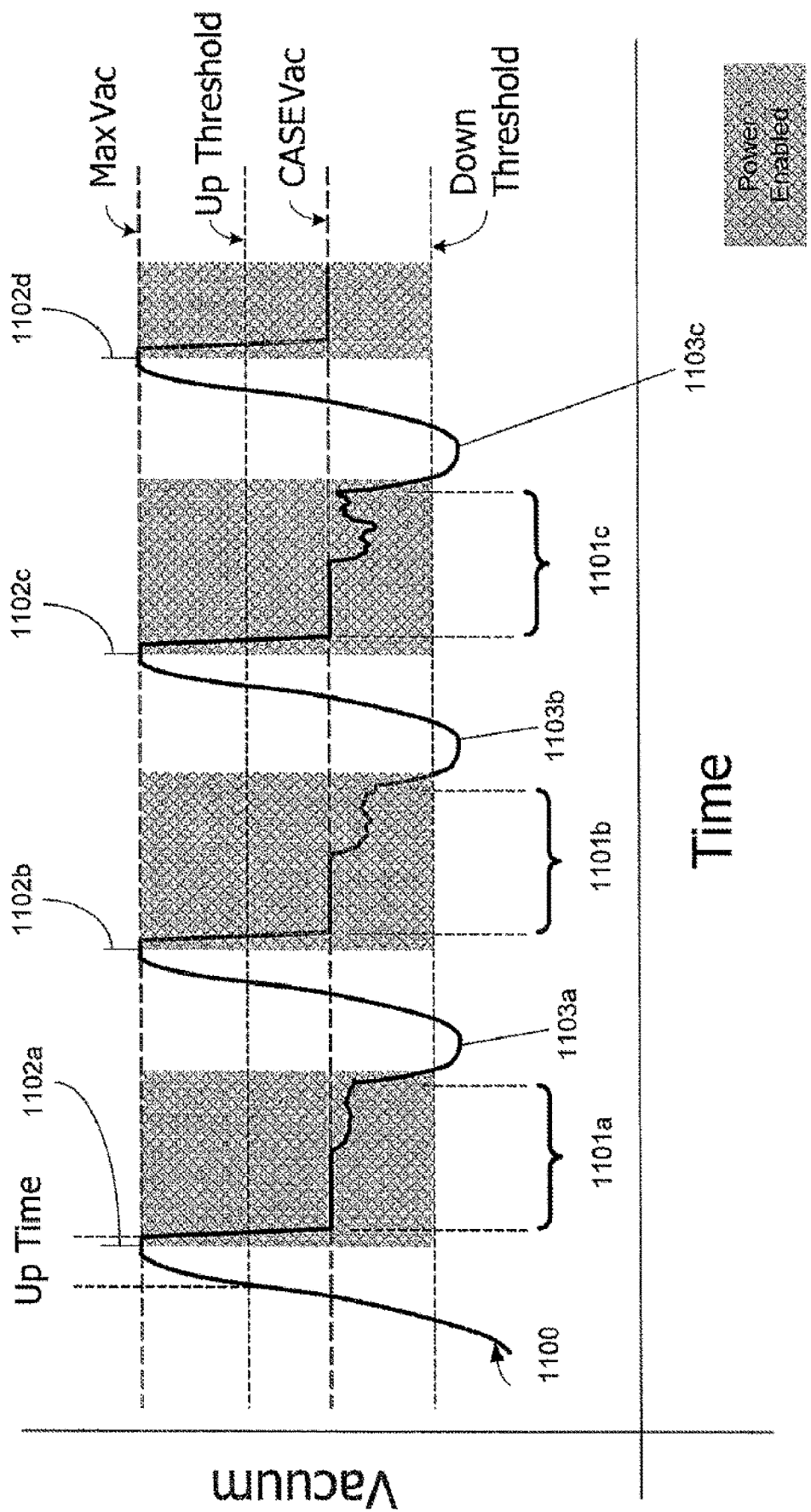
FIG. 11 shows representative operation of the present system in the presence of multiple occlusions, with a controllable down time employed.

FIG. 11 illustrates operation of the present system in the presence of multiple occlusions, with a controllable period of energy application after attaining Max Vac. In general, energy is applied until a predetermined amount of time passes, or alternately until vacuum pressure 1100 achieves a predetermined level. Max Vac or CASE Vac in these circumstances may vary, but in general the down time or time vacuum pressure 1100 drops can be mandated. From FIG. 11, vacuum pressure 1100 achieves Max Vac for a predetermined period of time, or attains Max Vac once and at a predetermined period thereafter, the system applies disruptive energy. In FIG. 11, Max Vac is attained at points 1102a, 1102b, 102c, and 1102d, and energy is applied a short time afterward, specifically a predetermined time after Max Vac has been initially achieved. FIG. 11 illustrates down times or energy application times 1101a, 1101b, and 1101c, which are predetermined in duration, and may be set by the surgeon or otherwise programmed in the phaco machine. These down times or energy application times 1101a, 1101b, and 1101c are time periods when disruptive energy is applied and their duration may depend on certain conditions or states of the machine (power settings for phaco application, etc.) As may be seen from FIG. 11, a long pulse or a lengthy time being held at CASE Vac may occur, causing deviation because perfect CASE Vac may not be held at all times. A period of neither energy application nor fluid pressure (vacuum pressure) occurs in this embodiment between the time energy is applied (regions 1101a, 1101b, and 1101c) and vacuum pressure applied, shown as points 1103a, 1103b, and 1103c.

It will be appreciated to those of skill in the art that the present design may be applied to other systems that perform tissue extraction, such as other surgical procedures used to remove hard nodules, and is not restricted to ocular or phacoemulsification procedures. In particular, it will be appreciated that any type of hard tissue removal, sculpting, or reshaping may be addressed by the application of pulsed fluid in the manner described herein.

Although there has been hereinabove described a method and apparatus for providing pulsed fluidics during a phacoemulsification procedure, for the purpose of illustrating the manner in which the invention may be used to advantage, it should be appreciated that the invention is not limited thereto. Accordingly, any and all modifications, variations, or equivalent arrangements which may occur to those skilled in the art, should be considered to be within the scope of the present invention as defined in the appended claims.

What is claimed is:

1. A surgical device comprising:
    a handpiece;
    a fluid line having a proximal end and a distal end, wherein the proximal end is operatively coupled to the handpiece;
    a pump operatively coupled to the distal end of the fluid line;
    a sensor operatively coupled to the fluid line in between the pump and the handpiece;
    a controller operatively coupled to the sensor, the controller configured to sense a change in fluid flow relative to a predetermined threshold, wherein upon sensing the fluid flow differs from the predetermined threshold, temporarily increasing aspiration vacuum pressure above a predetermined upper threshold to a maximum vacuum level (Max Vac) by operating the pump, wherein the Max Vac is greater than an occlusion threshold, and maintaining the aspiration vacuum pressure at the Max Vac from a first point in time to a second point in time; wherein the first point in time occurs while the aspiration vacuum pressure is at approximately the Max Vac and the second point in time occurs before an occlusion breaks; and
    an energy application device configured to apply electrically generated disruptive energy to a surgical site commencing at a third point in time at a nonzero predetermined time interval after aspiration vacuum pressure reaches the Max Vac and ceasing application of the electrically generated disruptive energy at a fourth point in time, wherein the fourth point in time occurs after aspiration vacuum pressure falls below a predetermined lower threshold and wherein the fourth point in time occurs after the occlusion breaks.

2. The surgical device of claim 1, wherein the handpiece is configured to provide ultrasonic energy to the surgical site generated by the energy application device.

3. The surgical device of claim 1, wherein the energy application device comprises a laser.

4. The surgical device of claim 1, wherein the energy application device comprises a device employing ultrasonic energy.

5. The surgical device of claim 1, wherein the surgical site comprises an ocular region, and the surgical device is employed to perform a phacoemulsification procedure.

6. The surgical device of claim 1, wherein the fluid line comprises an aspiration line.

7. The surgical device of claim 1, wherein the fluid line comprises an irrigation line.

8. The surgical device of claim 1, wherein the handpiece comprises the energy application device.

9. The surgical device of claim 1, wherein the change in fluid flow relative to the predetermined threshold indicates an occlusion within the surgical site.

10. The surgical device of claim 1, wherein the second point in time occurs after the third point in time.

* * * * *